US008637047B2

(12) United States Patent
Swart et al.

(10) Patent No.: US 8,637,047 B2
(45) Date of Patent: Jan. 28, 2014

(54) ERYSIPELOTHRIX RHUSIOPATHIAE-HAEMOPHILUS PARASUIS VACCINE AND METHODS OF USING THE SAME

(75) Inventors: John Randall Swart, Orange City, IA (US); Eric Martin Vaughn, Ames, IA (US); Karen E. Freking, Hospers, IA (US); Michael B. Roof, Ames, IA (US); Phillip Wayne Hayes, Maurice, IA (US); Reid C. Phillips, Parkville, MO (US)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 1455 days.

(21) Appl. No.: 10/975,702

(22) Filed: Oct. 28, 2004

(65) Prior Publication Data

US 2006/0093622 A1    May 4, 2006

Related U.S. Application Data

(60) Provisional application No. 60/515,860, filed on Oct. 30, 2003.

(51) Int. Cl.
*A61K 39/116* (2006.01)
*A61K 39/102* (2006.01)

(52) U.S. Cl.
USPC .................. 424/203.1; 424/184.1; 424/234.1; 424/256.1

(58) Field of Classification Search
USPC .......... 424/184.1, 190.1, 192.1, 203.1, 256.1, 424/234.1; 530/350, 825, 806; 435/975, 435/7.1; 514/2
See application file for complete search history.

(56) References Cited

U.S. PATENT DOCUMENTS

| | | | | |
|---|---|---|---|---|
| 6,013,266 | A * | 1/2000 | Segers et al. | 424/234.1 |
| 6,019,984 | A * | 2/2000 | MacInnes et al. | 424/255.1 |
| 6,342,231 | B1 * | 1/2002 | Burkhardt et al. | 424/256.1 |
| 6,559,282 | B1 * | 5/2003 | Wang | 530/324 |
| 7,172,762 | B1 * | 2/2007 | Roberts et al. | 424/234.1 |

OTHER PUBLICATIONS

Kitajima et al , J.Vet.Med.Sci.60 (1) :9-14, 1998.*
Product insert , Ingelvac HPE-1 from Boehringer and Ingelheim.*
PNEU PARAPAC ® +ER ) Or AR-PARAPAC® +0 ER(product insert ).*
By Roof M Bet al 2000, Proc.Int.Pig Vet.Soc.Congress (16 Meet., 658, 2000) Tab. 3 Ref.1.*
Yamazaki et al (Journal of Veterinary Medicine series B 1999, vol. 46, p. 47-55).*
Riising H J et al 1994, Int.Pig Vet.Soc.Congress (13 Meet., 228, 1994).*
Thomas et al Clinical Immunology vol. 105, Issue 3, Dec. 2002, pp. 259-272.*
Lacave et al 2001, Veterinary Microbiology, 80:247-253.*
Does stress-free livestock mean safer food?, http://www.foodnavigator.com/Financial-Industry/Does-stress-free-livestock-mean-safer-food, Jun. 4, 2004.
Vaccination Guidelines for Swine, VIDO Swine Technical Group—Linking knowledge to practical solutions, Vaccination Guidelines, www.vido.org, Jun. 2004.
Product Insert, Ingelvac HP-1; 2 pgs, 2006.
Title 9 Code of Federal Regulations, Part 112.7(f)(2), Jun. 2, 2010.
Veterinary Services Memorandum No. 800.203, USDA, Jan. 2006.

* cited by examiner

*Primary Examiner* — Padma V Baskar
(74) *Attorney, Agent, or Firm* — Michael P. Morris; Joyce L. Morrison

(57) ABSTRACT

The present invention provides a composition and an improved single dose vaccine against *E. rhusiopathiae* and an improved single dose vaccine against *E. rhusiopathiae* and *H. parasuis* which provides one or more of the following: 1) confers effective immunity against *E. rhusiopathiae* and/or *H. parasuis*; 2) decreases the risk of developing clinical signs of *E. rhusiopathiae* and/or *H. parasuis* infection; 3) induces an immune response against *E. rhusiopathiae* and/or *H. parasuis*; and 4) has a DOI against *E. rhusiopathiae* and/or *H. parasuis* of at least four months. The composition or *E. rhusiopathiae* vaccine as well as the combined *E. rhusiopathiae*-*H. parasuis* composition or vaccine each includes a bacterial component of inactivated *E. rhusiopathiae* bacteria and a suitable adjuvant. The combined *E. rhusiopathiae*-*H. parasuis* composition or vaccine further includes an amount of *H. parasuis* antigen. The vaccines can be administered to animals in any conventional manner. The amount of the dose for intramuscular administration is preferably less than 5 ml. The amount of *E. rhusiopathiae* and/or *H. parasuis* antigen in each dose should be enough to induce an immune response in the animal receiving the vaccine or composition and will preferably confer effective immunity against and decrease the risk of developing clinical signs resulting from *E. rhusiopathiae* and/or *H. parasuis* infection for a suitable duration of immunity.

20 Claims, No Drawings

ERYSIPELOTHRIX RHUSIOPATHIAE-HAEMOPHILUS PARASUIS VACCINE AND METHODS OF USING THE SAME

RELATED APPLICATIONS

This application claims the benefit of provisional application Ser. No. 60/515,860 filed on Oct. 30, 2003, the teachings and content of which are incorporated by reference herein.

BACKGROUND OF THE INVENTION

1. Field of the Invention

The present invention is concerned with a vaccine for *Erysipelothrix Rhusiopathiae* (*E. rhusiopathiae*) and a vaccine for *Haemophilus Parasuis* (*H. parasuis*). More particularly, the present invention is concerned with a vaccine for conferring effective immunity against *E. rhusiopathiae* and *H. parasuis* and methods of making the same. Still more particularly, the present invention is concerned with a vaccine which can be administered in a single dose and provide a duration of immunity (DOI) of a desired length. Even more particularly, the present invention is concerned with a single dose vaccine which provides a DOI equivalent to the average life span of an animal receiving the vaccine.

2. Description of the Prior Art

*E. rhusiopathiae* is a gram-positive bacteria that is pathogenic to over 50 species of vertebrate and invertebrate animals including swine, sheep, lambs, cattle, ducks, turkeys, and humans. *H. parasuis* is a gram-negative bacteria that is pathogenic to many animals, most notably swine. Vaccines against *E. rhusiopathiae* and *H. parasuis* are typically separate and consist of multiple doses given over the life span of an animal in order to confer effective immunity against *E. rhusiopathiae* and *H. parasuis*. There currently exists a vaccine against *H. parasuis* which can be administered in a single dose but a separate vaccination against *E. rhusiopathiae* must still be given. As is well known in the art, problems with vaccines that require more than one dose include the time and expense needed to track which animals have received first and/or second or subsequent doses, to track when the first dose was given, to do the actual vaccination, the increased size of the animals between first and subsequent doses, the increased risk of injury to the animal and to the person giving the subsequent doses of vaccine, and the expense associated with providing multiple doses.

What is needed in the art is a 1-dose regimen which confers effective immunity to an animal receiving the vaccination wherein the vaccine provides an extended DOI longer than is presently available through vaccines. What is further needed is a vaccine against *E. rhusiopathiae* that is administered in a single dose and provides a DOI of about six months. What is still further needed is a vaccine against *E. rhusiopathiae* and *H. parasuis* that provides a DOI of about six months after just a single dose of the vaccine.

SUMMARY OF THE INVENTION

The present invention overcomes the deficiencies of the prior art and provides a distinct advance in the state of the art. In particular, the present invention provides a vaccine which can be administered in a single dose and which provides one or more of the following: 1) confers effective immunity against *E. rhusiopathiae;* 2) decreases the risk of developing clinical signs of *E. rhusiopathiae* infection; 3) induces an immune response against *E. rhusiopathiae*; and 4) has a DOI of at least four months, more preferably at least about five months, and most preferably at least about six months. The present invention also provides a combination vaccine that provides one or more of the following: 1) confers effective immunity against *E. rhusiopathiae* and/or *H. parasuis;* 2) decreases the risk of developing clinical signs of *E. rhusiopathiae* and/or *H. parasuis* through a single dose of vaccine; 3) induces an immune response against *E. rhusiopathiae* and/or *H. parasuis*; and 4) provides a DOI against *E. rhusiopathiae* and/or *H. parasuis* of at least about four months, more preferably at least about 132 days, more preferably at least about 5 months, and most preferably at least about six months or at least about 162 days. Preferably, the combination vaccine can also be given as a single dose.

The *E. rhusiopathiae* vaccine includes a bacterial component of inactivated *E. rhusiopathiae* bacteria and a suitable adjuvant. The adjuvant can be selected based on the method of administration and may include mineral oil-based adjuvants such as Freund's complete and incomplete adjuvant, Montanide incomplete Seppic adjuvant such as ISA, oil in water emulsion adjuvants such as the Ribi adjuvant system, syntax adjuvant formulation containing muramyl dipeptide, oraluminum salt adjuvants. Preferably, the adjuvant is a mineral oil-based adjuvant, most preferably ISA206 (SEPPIC, Paris, France). The composition may also include any one or combination of pharmaceutically acceptable carriers or excipients including, but not limited to, buffers, stabilizers, diluents, preservatives, and solubilizers. The vaccine is administered to animals susceptible to infection by *E. Rhusiopathiae*, preferably mammals, and still more preferably pigs, in any conventional manner, including oral, intranasal, intramuscular, intra-lymph node, intradermal, intraperitoneal, subcutaneous, and combinations thereof, but most preferably through intramuscular (IM) injection. The amount of the dose for intramuscular administration is preferably up to about 5 ml, still more preferably between 1 ml and 3 ml, and most preferably about 2 ml.

The combined *E. rhusiopathiae-H. parasuis* vaccine includes inactivated bacterial components of both *E. rhusiopathiae* and *H. parasuis*, together with a suitable adjuvant. Preferably, the adjuvant is mineral-oil based, most preferably ISA206. The vaccine is administered to animals susceptible to infection by *E. rhusiopathiae* and/or *H. parasuis*, preferably mammals, and still more preferably pigs, in any conventional manner, including oral, intranasal, intramuscular, intra-lymph node, intradermal, intraperitoneal, subcutaneous, and combinations thereof, most preferably through intramuscular (IM) injection. The amount of the dose when IM injection is the selected administration route is preferably up to about 5 ml, still more preferably between 1 ml and 3 ml, and most preferably about 2 ml. The amount of *E. rhusiopathiae* antigen in each dose should be enough to confer effective immunity against and decrease the risk of developing clinical signs resulting from *E. rhusiopathiae* infection to an animal receiving a vaccination therewith. Preferably the amount of *E. rhusiopathiae* antigen should be up to about 5 ml, more preferably between about 0.2 to 3 ml, still more preferably between about 0.3 to 1.5 ml, more preferably between about 0.4 to 0.8 ml, and still more preferably about 0.6 ml. The amount of *H. parasuis* antigen in each dose should be up to about 5 ml, more preferably between about 0.1 to 3 ml, still more preferably between about 0.15 to 1.5 ml, more preferably between about 0.2 to 0.6 ml, and still more preferably about 0.4 ml. In a different form of measurement, the amount of *H. parasuis* antigen in each dose should contain at least $1.5 \times 10^7$ cfu/dose, more preferably between about $1.5 \times 10^8$ to $1.5 \times 10^{10}$ cfu/dose and still more preferably about $1.5 \times 10^9$ cfu/dose. In a particularly preferred 2 ml dose, approximately 0.6 ml is *E. rhusiopathiae* antigen, approximately 1.0 ml is the adjuvant and approximately 0.4 ml is the *H. parasuis* antigen. Preferably, the bacteria are inactivated by conventional inactivation techniques and especially conventional formalin inactivation techniques.

Vaccines and compositions of the present invention are generally useful for inducing immune responses in animals as immune response-stimulating therapeutics or prophylactic vaccines. Preferably, administration of the compositions or vaccines of the present invention results in an immune response that protects the vaccinated animal in various ways including a lessening in the severity or delay in the onset of clinical signs of E. rhusiopathiae and/or H. parasuis infection. Still more preferably, administration of the compositions or vaccines results in a reduced risk of developing clinical signs of E. rhusiopathiae and/or H. parasuis infection, even after exposure or challenge by virulent forms of E. rhusiopathiae and/or H. parasuis. In particularly preferred forms, administration of the composition or vaccine results in a complete prevention of these clinical signs.

Various conventional methods can be used to determine if an immune response was induced in an animal. For example, the animal receiving the composition or vaccine can be challenged with a virulent form of E. rhusiopathiae and/or H. parasuis and observed for the development of clinical signs of infection for a period of time after challenge. An alternative method of determining if an immune response was induced by administration of the composition or vaccine would be to assay a biological sample from the animal for antibodies to one or more antigens of E. rhusiopathiae and/or H. parasuis. Such methods are common in the field and appropriate antibody assays could be determined by those of skill in the art.

DETAILED DESCRIPTION OF THE PREFERRED EMBODIMENT

The following examples set forth preferred embodiments of the present invention. It is to be understood that these examples are provided by way of illustration and nothing therein should be taken as a limitation upon the overall scope of the invention.

EXAMPLE 1

This example provides data as to the efficacy and duration of immunity against virulent E. rhusiopathiae following a preferred single dose H. parasuis-E. rhusiopathiae vaccine.

Materials and Methods

A total of 37 pigs aged 3 to 4 weeks, none of which had been previously vaccinated with Erysipelothrix bacterins or vaccines, were used for the study leading to this example. Throughout the study, the animals were provided food sufficient for their size, age and other physical characteristics. Water was supplied ad libitum. The animals were housed in confinement swine facilities with full or partially slatted floors, mechanical ventilation, and supplemental heat and light appropriate for the age of the animals.

Two days prior to the study, all of the pigs were given a health exam and vaccinated for Pseudorabies Virus. On day 1 of the study, the pigs were divided into two groups. Group 1 was composed of 23 pigs that received one 2 mL intramuscular dose of H. parasuis-E. rhusiopathiae Bacterin with adjuvant ISA 206 ("HPE") (Boehringer Ingelheim Vetmedica, Inc., St. Joseph, Mo.) in the left neck on day 1. The E. rhusiopathiae antigen was included in each dose at the rate of 0.6 mL volume of harvest antigen. Group 2, the control group, was composed of 14 pigs that received no treatment at all. On days 21, 54 and 161 of the study, all of the animals were bled to monitor seroconversion to vaccination.

On day 162 of the example, all of the pigs (except for 3 who had died from incidental causes prior to day 162) were challenged with a virulent strain of E. rhusiopathiae EL-6P. All of the pigs were then observed for seven days for general health and the clinical signs of E. rhusiopathiae. On day 7 following the challenge, all of the animals were euthanized and those showing persistent clinical signs and/or elevated body temperature for 2 consecutive days typical of E. rhusiophatiae as set forth in 9 CFR 113.67 were necropsied. A necropsy was also performed on all of the animals that died during the trial. Gross lesions were assessed and recorded, and tissues were collected and sent to a laboratory for bacterial culture.

A summary of the above protocol can be found in Table 1.

TABLE 1

| Day | Event |
| --- | --- |
| 1 | Pigs randomized and assigned to groups. Group 1 pigs received HPE and Group 2 received the non-vaccinated control treatment. |
| 21 | All pigs bled. |
| 54 | All pigs bled. |
| 160-169 | Daily observation and body temperature 2 days before challenge and 7 days post challenge. |
| 161 | All pigs bled. |
| 162 | Pigs challenged with E. rhusiopathiae EL-6P serial #3. |
| 169 | End of trial. |

Results and Discussion:

All 13 of the pigs from Group 2 were affected and showed elevated body temperature greater than 106.5° F., clinical signs of infection by E. rhusiopathiae, or death after challenge with virulent E. rhusiopathiae. E. rhusiopathiae was recovered from 9 of the 13 pigs from Group 2, and 6 of the 13 pigs from Group 2 died following the challenge. In contrast, 20 of the 21 pigs from Group 1 remained healthy and were protected from the virulent challenge of E. rhusiopathiae 162 days post vaccination. None of the pigs from Group 1 died following the challenge. There was no E. rhusiopathiae recovered from the single Group 1 pig that did not remain healthy following challenge. Table 2 contains morbidity results and analysis while Table 3 contains mortality results.

TABLE 2

Morbidity

| | # Pigs Affected by E. Rhusiopathiae | # Pigs Protected from E. Rhusiopathiae | Total # Pigs |
| --- | --- | --- | --- |
| Group 1 | 1 | 20 | 21 |
| Group 2 | 13 | 0 | 13 |

| | Chi-Square | P-Value |
| --- | --- | --- |
| Uncorrected: | 23.28 | .0000014 |
| Mantel-Haenszel: | 22.42 | .0000022 |
| Yates corrected: | 19.71 | .000009 |

TABLE 3

Mortality

| | # Pigs Died After Challenge | # Pigs Survived After Challenge | Total # Pigs |
| --- | --- | --- | --- |
| Group 1 | 0 | 21 | 21 |
| Group 2 | 6 | 7 | 13 |

TABLE 3-continued

| Mortality | | |
|---|---|---|
| | Chi-Square | P-Value |
| Uncorrected: | 11.77 | .0006 |
| Mantel-Haenszel: | 11.42 | .0007 |
| Yates corrected: | 8.81 | .0029 |

Vaccinates challenged with virulent *E. rhusiopathiae* 162 days after vaccination were well protected when compared to controls. 100% of the non-vaccinated controls developed the disease and 46% died following the challenge. By contrast, a single does of the HPE protected 95% of the challenged pigs and none of the pigs that received the vaccine died following challenge. The results of this study confirm the duration of immunity of at least 162 days for the HPE in a single dose regimen for prevention and control of erysipelas in nursery pigs aged 3 weeks of age or older.

EXAMPLE 2

This example demonstrates the duration of immunity of a preferred single dose vaccine against virulent *H. parasuis* challenge after vaccination.

Materials and Methods:

The study for this example began with 36 pigs aged 3 to 4 weeks, none of which had been previously vaccinated using *H. parasuis* bacterin or vaccine. Throughout the example, the animals were provided food sufficient for their size, age and other physical characteristics. Water was supplied ad libitum.

On day 1 of the example, the pigs were divided into two groups. Group 1 was composed of 23 pigs that received one 2 mL intramuscular dose of *H. parasuis* Bacterin with adjuvant ISA 206 ("HPB") (Boehringer Ingelheim Vetmidica, Inc., St. Joseph, Mo.) on day 1. The *H. parasuis* antigen was included in each dose at the rate of $1.5 \times 10^9$ cfu/dose. Group 2, the control group, was composed of 13 pigs who received no treatment at all.

On day 132 of the example, 11 pigs from Group 2 and 17 of the pigs from Group 1 were healthy and suitable for challenge with a virulent strain of *H. parasuis*. The 8 pigs (6 from Group 1 and 2 from Group 2) that did not receive challenge were unhealthy or had died for reasons unrelated to vaccination. All of the pigs were then observed for seven days for general health and the clinical signs of *H. parasuis*. A necropsy was performed on all of the animals that died during the trial and tissues were taken for bacterial confirmation of the cause of death when deemed necessary. On day 7 following the challenge, all of the animals were euthanized and those showing persistent clinical signs and/or elevated body temperature for 2 consecutive days typical of *H. parasuis* were necropsied. Gross lesions were assessed and recorded, and tissues were collected and sent to a laboratory for bacterial culture.

A summary of the above protocol can be found in Table 4.

TABLE 4

| Day | Event |
|---|---|
| 1 | Pigs randomized and assigned to groups. Group 1 pigs received HPB and Group 2 received the non-vaccinated control treatment. |
| 130-139 | Daily observation and body temperature 2 days before challenge and 7 days post challenge. |
| 132 | Pigs challenged with *H. parasuis*. |
| 139 | End of trial. |

Results and Discussion:

Clinical signs of *H. parasuis* infection was shown by 8 of 11 pigs of the control group and necropsy showed that 7 of the 11 had post mortem lesions typical of *H. parasuis*. A total of 6 control pigs died after challenge, and 5 of these 6 had gross lesions typical of *H. parasuis*. Severe clinical signs resulting in terminal recumbency for two or more days developed in two more pigs. These pigs also had lesions typical of *H. parasuis* at necropsy. Of the 8 affected control pigs, 6 were positive for *H. parasuis* on bacterial culture. The 3 remaining pigs did not show any signs of disease due to *H. parasuis*.

In contrast, 16 of the 17 pigs from Group 1 were protected from the virulent challenge of *H. parasuis* 132 days post vaccination. One of the pigs from Group 1 died following the challenge. There was no *H. parasuis* recovered from the single Group 1 pig who died following challenge, however, it did have post mortem lesions consistent with the occurrence of the disease. Table 5 contains morbidity results and analysis while Table 6 contains mortality results.

TABLE 5

| Morbidity | | | |
|---|---|---|---|
| | # Pigs Affected by *H. parasuis* | # Pigs Protected from *H. parasuis* | Total # Pigs |
| Group 1 | 1 | 16 | 17 |
| Group 2 | 8 | 3 | 11 |
| | Chi-Square | P-Value | |
| Uncorrected: | 13.68 | .0002 | |
| Mantel-Haenszel: | 13.19 | .0003 | |
| Yates corrected: | 6.04 | .0139 | |

TABLE 6

| Mortality | | | |
|---|---|---|---|
| | # Pigs Died After Challenge | # Pigs Survived After Challenge | Total # Pigs |
| Group 1 | 1 | 16 | 17 |
| Group 2 | 6 | 5 | 11 |
| | Chi-Square | P-Value | |
| Uncorrected: | 8.43 | .0037 | |
| Mantel-Haenszel: | 8.13 | .0043 | |
| Yates corrected: | 6.04 | .0139 | |

Vaccinates challenged with virulent *H. parasuis* 132 days after vaccination were well protected when compared to controls. 73% of the non-vaccinated controls developed the disease and 55% died following the challenge. By comparison, a single dose of the HPB protected 94% of the challenged pigs. The vaccinates also experienced statistically significant lower mortality than controls due to *H. parasuis*. The results of this example confirm the duration of immunity of at least 132 days for the HPB in a single dose regimen in nursery pigs aged 3 weeks of age or older.

EXAMPLE 3

This example describes a preferred method of preparing vaccine in accordance with the present invention.

Materials and Methods:

The composition of the *E. rhusiopathiae-H. parasuis* Bacterin includes strains SE-9 and Z-1517 of *E. rhusiopathiae* and *H. parasuis*, respectively. These strains have been deposited with the ATCC and have been assigned deposit numbers PTA-6261 and PTS-6262, respectively. The seed materials of each are identified by characteristic growth patterns, Gram's stain reactions and biochemical tests. The virulence of the seed materials is determined by the ability to kill mice and/or produce clinical signs in susceptible swine.

The composition of the growth media for *E. rhusiopathiae* is found in Table 7. The composition of the growth media for *H. parasuis* is found in Table 8.

TABLE 7

|  | Ingredient | Amount |
|---|---|---|
| VPI Salts Solution | Anhydrous Calcium Chloride | 0.2 g |
|  | Anhydrous Magnesium Sulfate | 0.2 g |
|  | Potassium Phosphate Monobasic | 1.0 g |
|  | Sodium Bicarbonate | 10.0 g |
|  | Sodium Chloride | 2.0 g |
|  | RO Water q.s | 1000.0 mL |
| 25% Dextrose Solution | Dextrose | 250. g |
|  | RO Water q.s | 1000.0 mL |
| Production Seed and Production Culture Media | Beef Paste | 2.0 g |
|  | Proteose Peptone 3 | 20.0 g |
|  | Sodium Phosphate Heptahydrate | 8.0 g |
|  | Bacto Yeast | 40.0 g |
|  | Dextrose | 8.167 g |
|  | Tween 80 | 1.36 mL |
|  | RO Water q.s | 1000.0 mL |

(note:
to prepare the Production Seed and Production Culture Media, the pH should be adjusted to 8.6 by adding 10N NaOH or 5N HCl and it should also be heat sterilized.)

TABLE 8

|  | Ingredient | Amount |
|---|---|---|
| 5% NAD Stock Solution for Media | B-Nicotinamide Adenine Dinucleotide | 5.0 g |
|  | L-Cysteine | 1.0 g |
|  | RO Water q.s | 100.0 mL |
| 2M Tris Solution | TRIS (hydroxymethyl) Amino Methane | 121.14. g |
|  | RO Water q.s | 500.0 mL |
| Production Seed Culture Media | Tryptic Soy Broth | 5.7 g |
|  | 3.6% SAG 730 Antifoam Solution | 1.8 mL |
|  | RO Water | 842.2 mL |
| Heat sterilize and aseptically add: | Sterile 10X Minimum Essential Medium Containing Non-Essential Amino Acids | 95.0 mL |
|  | 15% Sterile Fresh Yeast Extract Solution | 9.6 mL |
|  | 5% NAD Stock Solution | 9.6 mL |
|  | Certified Newborn Bovine Calf Serum | 38.0 mL |
|  | 2M Tris Solution | 2.2 mL |

(note:
5% NAD Stock Solution should be filter sterilized through 0.2 micron filter and stored frozen. 2M Tris Solution should be heat sterilized and stored cool.)

The strains of both *E. rhusiopathiae* and *H. parasuis* seed cultures should be grown in 500 to 20,000 mL vessels. Their production cultures are grown in 20-1000 L vessels. Master and Working Seeds of both strains should be stored frozen at <−60° C.

To prepare suspensions of *E. rhusiopathiae* for seeding or inoculation, the Master seed is returned to the liquid phase and 1 to 2 mL is inoculated into Working Seed Culture Media. The culture is then grown statically at 34-38° C. for 6 to 24 hours. The cultures are then checked for purity by colony appearance on 5% sheep blood agar, cell morphology, and Gram's stain. An equal volume of stabilizer is added and dispensed into cryotubes for storage.

To prepare suspensions of *H. parasuis* for seeding or inoculation, the Master seed is returned to the liquid phase and is inoculated into Working Seed Culture Media. The culture is then stirred at 34-38° C. for 12 to 18 hours. The cultures are then checked for purity by colony appearance on 5% sheep blood agar, cell morphology, and Gram's stain. An equal volume of stabilizer is added and dispensed into cryotubes for storage.

To inoculate *E. rhusiopathiae,* 1-12 mL of Working Seed are inoculated into a glass vessel containing 500 to 18,000 mL media to prepare Production Seed. Up to 5% (v/v) Production Seed is inoculated into 15 to 750 L of media in 20 to 1000 L vessels to prepare Production Culture. Production Cultures are checked for purity by streaking on 5% sheep blood agar, incubating at 34-38° C. for 24-48 hours and observing colony morphology.

To inoculate *H. parasuis,* 1-10 mL of Working Seed are inoculated into a glass vessel containing 500 to 18,000 mL media to prepare Production Seed. Up to 7% (v/v) Production Seed is inoculated into 14 to 750 L of media in 20 to 1000 L vessels to prepare Production Culture. Production Cultures are checked for purity by streaking on 5% sheep blood agar, supplemented with NAD streak, incubating at 34-38° C. for 18-24 hours, and observing colony morphology.

For the incubation of *E. rhusiopathiae*, Seed Cultures are incubated at 34-38° C. for 6 to 24 hours aerobically. Production Cultures are incubated at 34-38° C. for 6 to 12 hours aerobically with optional agitation. For the incubation of *H. parasuis*, Seek and Production Cultures are incubated at 34-38° C. for 6 to 18 hours while stirring and with optional sparging with compressed air.

During the growth period for *E. rhusiopathiae*, pH is controlled by 2M Tris and the cultures are observed macroscopically during the incubation period for evidence of abnormal growth or signs of contamination. The media is turbid prior to inoculation. As growth increases, settling will be observed. Samples are taken to determine % transmittance. Purity is determined by colony morphology on 5% sheep blood agar and/or Gram's stain. A macroscopic observation of sufficient turbidity indicates that the culture is ready for harvest. This will occur between 6-12 hours following inoculation of Production Culture.

For *H. parasuis*, cultures are observed macroscopically during the incubation period for evidence of abnormal growth or signs of contamination. Samples are taken to determine direct counts. Purity is determined by colony morphology on 5% sheep blood agar supplemented with an NAD streak and/or Gram's stain. A macroscopic observation of sufficient turbidity and a drop in pH (<7.0) indicates that a culture is ready for harvest. This will occur between 6-12 hours following inoculation of Production Culture.

For both strains, each Production Culture is sampled for purity testing and percent transmittance and each Production Culture vessel is prepared for inactivation. For *E. rhusiopathiae*, Production Cultures must exhibit typical growth as described, have a percent transmittance of <40% at 620 nm, and be free of any evidence of contamination. For *H. parasuis*, Production Cultures will have a microscopic count of $>5\times10^7$ organisms/mL and will be free of any evidence of contamination.

Both strains are inactivated by the addition of formalin to the Production Cultures up to 0.5% (v/v). Inactivation is performed at 20-38° for 12-72 hours with optional agitation. The inactivated product is then stored at 2 to 7° C. Inactivation is confirmed by standard techniques.

Adjuvant ISA 206 is added at 30-65% (w/v). The inactivated cultures are emulsified by homgenization with ISA 206. Sodium bisulfite solution 35% may be added to fractions or product to neutralize free formaldehyde. Formaldehyde solution may be added to fractions or at assembly of product not to exceed 0.2% concentration in completed product.

The resulting products can then be concentrated in a sterile closed loop system utilizing a hollow fiber filtration with a 100,000 molecular weight cut off or by aseptically decanting settled culture to provide a concentration up to $2\times10^{10}$ organisms/mL.

*E. rhusiopathiae* is standardized by percent transmittance and concentration. *H. parasuis* is standardized by direct count of organisms.

EXAMPLE 4

This example demonstrates the assembly of the different vaccine components into a preferred vaccine in accordance with the present invention.

Materials and Methods:

Vaccine in accordance with the present invention can be made by combining 90,000 mL *E. rhusiopathiae* culture (which represents 90,000 mL of *E. rhusiopathiae* culture at 40% transmittance), 56,250 mL *H. parasuis* culture (which represents 56,250 mL of $4\times10^9$ organisms/mL *H. parasuis* culture), 2,250 mL sterile RO water, 150,000 mL ISA 206, and 1,500 mL sterile 35% sodium bisulfate solution. Sterile 35% sodium bisulfate solution is also used as needed to neutralize formaldehyde levels to 0.2% formaldehyde solution. The pH of the resulting mixture is adjusted to 6.2-7.2 by the addition of ION sodium hydroxide or 5N hydrochloric acid as needed.

Such a mixture should provide *E. rhusiopathiae* in a concentration equivalent to 0.3-0.9 mL of Harvest Culture at 40% transmittance and at least $1.5\times10^{9}$ *H. parasuis* organisms in each 2 mL dose.

We claim:

1. A composition comprising:

an amount of bacterin from *Erysipelothrix Rhusiopathiae* strain SE-9 serotype 2, PTA 6261;

an amount of bacterin from *Haemophilus Parasuis* strain Z-1517, PTA 6262; and an adjuvant, comprising ISA 206, said composition providing animals receiving said composition a reduced risk of developing clinical signs of infection from *Erysipelothrix Rhusiopathiae* and *Haemophilus Parasuis* for at least 4 months after receiving a single administration of said composition.

2. The composition of claim 1, said amount of *Erysipelothrix Rhusiopathiae* bacterin in said composition being an amount effective at reducing the risk of developing clinical signs of *Erysipelothrix Rhusiopathiae* infection when administered to an animal susceptible to *Erysipelothrix Rhusiopathiae* infection.

3. The composition of claim 2, said effective amount of *Erysipelothrix Rhusiopathiae* bacterin being up to about 5 ml.

4. The composition of claim 1, said amount of bacterin from *Haemophilus Parasuis* being an amount effective at reducing the risk of developing clinical signs of *Haemophilus Parasuis* infection when administered to an animal susceptible to *Haemophilus Parasuis* infection.

5. The composition of claim 4, said effective amount of *Haemophilus Parasuis* being up to about 5 ml.

6. The composition of claim 4, said effective amount of *Haemophilus Parasuis* bacterin containing at least $1.5\times10^{7}$ cfu/dose.

7. The composition of claim 1, said adjuvant having a mineral oil base.

8. The composition of claim 1, said composition being effective at inducing an immune response against infection from a pathogen selected from the group consisting of *Haemophilus Parasuis, Erysipelothrix Rhusiopathiae*, and combinations thereof.

9. A vaccine for reducing the risk of developing clinical signs of *Erysipelothrix Rhusiopathiae* infection after a single administration of said vaccine, said vaccine comprising:

an amount of *Erysipelothrix Rhusiopathiae* strain SE-9 serotype 2, PTA 6261 bacterin, an amount of *Haemophilus Parasuis* strain Z-1517, PTA 6262 bacterin and an adjuvant, comprising ISA 206, wherein said vaccine reduces the risk of developing clinical signs of *Erysipelothrix Rhusiopathiae* for at least 4 months after said administration.

10. The vaccine of claim 9, said amount of *Erysipelothrix Rhusiopathiae* bacterin being up to about 5 ml.

11. The vaccine of claim 9, said amount of bacterin from *Haemophilus Parasuis* being an amount effective at reducing the risk of developing clinical signs of *Haemophilus Parasuis* infection.

12. The vaccine of claim 9, said amount of *Haemophilus Parasuis* bacterin being up to about 5 ml.

13. The vaccine of claim 9, said effective amount of *Haemophilus Parasuis* bacterin containing at least $1.5\times10^{7}$ cfu/dose.

14. The vaccine of claim 9, said adjuvant having a mineral oil base.

15. The vaccine of claim 9, said vaccine reducing the risk of developing clinical signs of *Erysipelothrix Rhusiopathiae* infection for at least four months following administration.

16. The vaccine of claim 9, said vaccine being effective at inducing an immune response against infection from a pathogen selected from the group consisting of *Haemophilus Parasuis, Erysipelothrix Rhusiopathiae*, and combinations thereof.

17. The composition of claim 1, said bacterin being whole cells from *Haemophilus Parasuis* or *Erysipelothrix Rhusiopathiae.*

18. The composition of claim 17, said whole cells being inactivated.

19. The vaccine of claim 9, said bacterin being whole cells from *Erysipelothrix Rhusiopathiae.*

20. The vaccine of claim 19, said whole cells being inactivated.

* * * * *

UNITED STATES PATENT AND TRADEMARK OFFICE
CERTIFICATE OF CORRECTION

| | | |
|---|---|---|
| PATENT NO. | : 8,637,047 B2 | Page 1 of 1 |
| APPLICATION NO. | : 10/975702 | |
| DATED | : January 28, 2014 | |
| INVENTOR(S) | : Swart et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1586 days.

Signed and Sealed this
Twelfth Day of May, 2015

Michelle K. Lee
*Director of the United States Patent and Trademark Office*